United States Patent [19]

Noda et al.

[11] Patent Number: 5,644,116
[45] Date of Patent: Jul. 1, 1997

[54] CARBON MONOXIDE SENSOR AND METHOD OF DETECTING CARBON MONOXIDE

[75] Inventors: Kazutoshi Noda, Tsukuba; Tetsuhiko Kobayashi; Masanori Ando, both of Ikeda, all of Japan

[73] Assignee: Director-General of Agency of Industrial Science and Technology, Japan

[21] Appl. No.: 681,501

[22] Filed: Jul. 23, 1996

[30] Foreign Application Priority Data

Jul. 26, 1995 [JP] Japan ................ 7-190222

[51] Int. Cl.[6] .......................... G01N 21/00; G01N 21/01
[52] U.S. Cl. ................ 204/157.15; 205/782; 205/782.5; 205/783
[58] Field of Search .................. 204/157.15; 205/782, 205/782.5, 783

[56] References Cited

FOREIGN PATENT DOCUMENTS 61-149855  7/1986  Japan .

Primary Examiner—Kathryn L. Gorgos
Assistant Examiner—Edna Wong
Attorney, Agent, or Firm—Lorusso & Loud

[57] ABSTRACT

A carbon monoxide sensor in the form of a composite material including a transparent substrate, and a metal oxide layer provided over a surface of the substrate and containing nickel oxide and cobalt oxide in an amount providing an atomic ratio Ni/Co of 99:1 to 1:2. Carbon monoxide contained in an oxygen-containing gas is detected by a change in transmittace of light with a wave length of 350–1,500 nm passing through the composite material maintained at a temperature of 200°–350° C.

1 Claim, 2 Drawing Sheets

CARBON MONOXIDE SENSOR AND METHOD OF DETECTING CARBON MONOXIDE

BACKGROUND OF THE INVENTION

This invention relates to a carbon monoxide sensor material and to a method of detecting carbon monoxide in a gas.

It is known that a metal oxide film of a positive-type semiconductor, such as a nickel oxide (NiO) film or a cobalt oxide ($Co_3O_4$) film, can absorb light with a wave length of 350–1,500 nm when contacted with an oxygen-containing gas at an elevated temperature. When a reducing gas such as carbon monoxide is present in the gas, the absorbance is reduced depending upon the concentration of the carbon monoxide. Thus, the metal oxide film might be used as a carbon monoxide sensor material. However, the sensitivity of the nickel oxide or cobalt oxide film to carbon monoxide is not good. Further, the response of such an oxide film to a change of the concentration of carbon monoxide is not fast. Therefore, the nickel oxide film and cobalt oxide film are not used in practice for the detection of carbon monoxide.

SUMMARY OF THE INVENTION

It is an object of the present invention to provide a novel carbon monoxide sensor material which has a high sensitivity to carbon monoxide and which can quickly respond to a change of the carbon monoxide concentration.

Another object of the present invention is to provide a method for detecting carbon monoxide.

In accomplishing the foregoing object, the present invention provides a composite material comprising a transparent substrate, and a metal oxide layer provided over a surface of said substrate and containing nickel oxide and cobalt oxide in an amount providing an atomic ratio Ni/Co of 99:1 to 1:2.

In another aspect, the present invention provides a method of detecting carbon monoxide in an oxygen-containing gas, comprising the steps of:

fixedly securing a sensor within a light permeable cell, said sensor comprising a transparent substrate, and a metal oxide layer provided over a surface of said substrate and containing nickel oxide and cobalt oxide in an amount providing an atomic ratio Ni/Co of 99:1 to 1:2;

feeding said gas through said sensor-containing cell;

irradiating said cell with light with a wave length of 350–1,500 nm while maintaining said sensor at a temperature of 200°–350° C., such that said light passes through said sensor contained in said cell; and measuring the transmittance of said light through said sensor.

BRIEF DESCRIPTION OF THE DRAWING

Other objects, features and advantages of the present invention will become apparent from the detailed description of the preferred embodiments of the invention which follows, when considered in light of the accompanying drawings in which.

DETAILED DESCRIPTION OF THE PREFERRED EMBODIMENTS OF THE INVENTION

Figure 1:
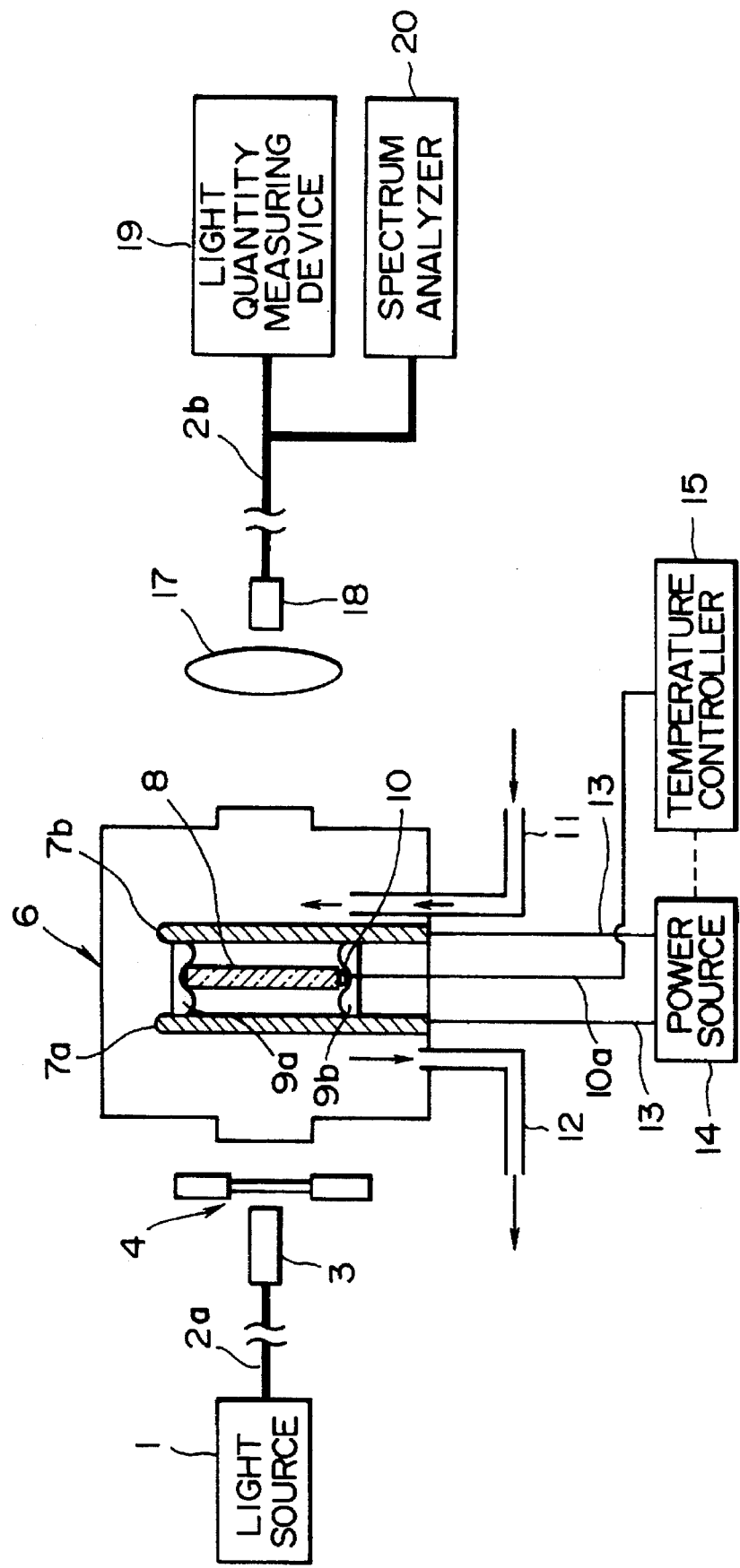
FIG. 1 is a schematic illustration of a device useful for carrying out the CO detection according to the present invention.

The carbon monoxide sensor material according to the present invention is a composite material having a transparent substrate, and a metal oxide layer provided over a surface of the substrate and containing nickel oxide and cobalt oxide in an amount providing an atomic ratio Ni/Co of 99:1 to 1:2.

The transparent substrate is preferably made of a heat resisting material which is substantially transparent to light with a wave length of 350–1,500 nm and which is chemically inert to oxygen and carbon monoxide. Examples of suitable transparent substrates include glass and quartz. The shape and thickness of the substrate is not specifically limited. Generally, however, the substrate is a flat plate having a thickness of 0.1–1 mm.

The metal oxide layer provided on a surface of the transparent substrate is formed of a mixed metal oxide containing Ni and Co in amounts providing an atomic ratio Ni/Co of 99:1 to 1:2, preferably 9:1 to 1:2. The thickness of the metal oxide layer is not specifically limited but is generally in the range of 0.1–1 mm.

The carbon monoxide sensor material may be prepared by forming the Ni-Co oxide layer on a surface of the transparent substrate by any suitable known manner. Preferably, the Ni-Co oxide layer may be formed by applying an organic solvent solution containing soluble nickel compound and soluble cobalt compound to a surface of the substrate, followed by drying of the coated layer and calcining of the dried layer in air at 350°–450° C. The soluble compound may be an organic acid salt or a chelate. Alternatively, the Ni-Co oxide layer may be formed by vacuum deposition.

The mechanism of the CO detection by the sensor material according to the present invention is perhaps as follows:

In the presence of oxygen, the metal oxide layer adsorbs oxygen to form a positive hole $P^+$:

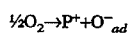

When the oxygen-adsorbed metal oxide layer is brought into contact with CO at an elevated temperature, the positive hole disappears:

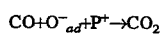

Since the decrease of the positive holes is proportional with the concentration of CO and since the absorbance of light by the metal oxide layer is proportional with the amount of the positive holes, it is possible to detect CO from the change in absorbance.

Thus, in one embodiment according to the present invention, carbon monoxide in an oxygen-containing gas is detected using the above sensor material as follows. The concentration of oxygen in the gas is generally in the range of 0.1–99.95% by volume. The sensor material is disposed within a light permeable cell, to which the gas is fed at a predetermined flow rate. The cell is irradiated with light having a wave length of 350–1,500 nm, preferably 500–1,500 nm, such that the light passes through the sensor disposed in the cell, while maintaining the sensor at a temperature of 200°–350° C., preferably 250°–300°C. As the light source, there may be used a halogen lamp, a fluorescent lamp or an incandescent lamp. The light from the light source is preferably passed through a collimating lens to form parallel rays. The incident light may be a monochromatic or polychromatic light. The transmitted light is received by a photoelectric converter such as a photoelectric tube or a photocell.

In quantitatively analyzing CO, it is desired to previously prepare a calibration or working curve showing the relationship between the CO concentration and transmittance using gas samples containing various known amounts of CO.

Figure 2:
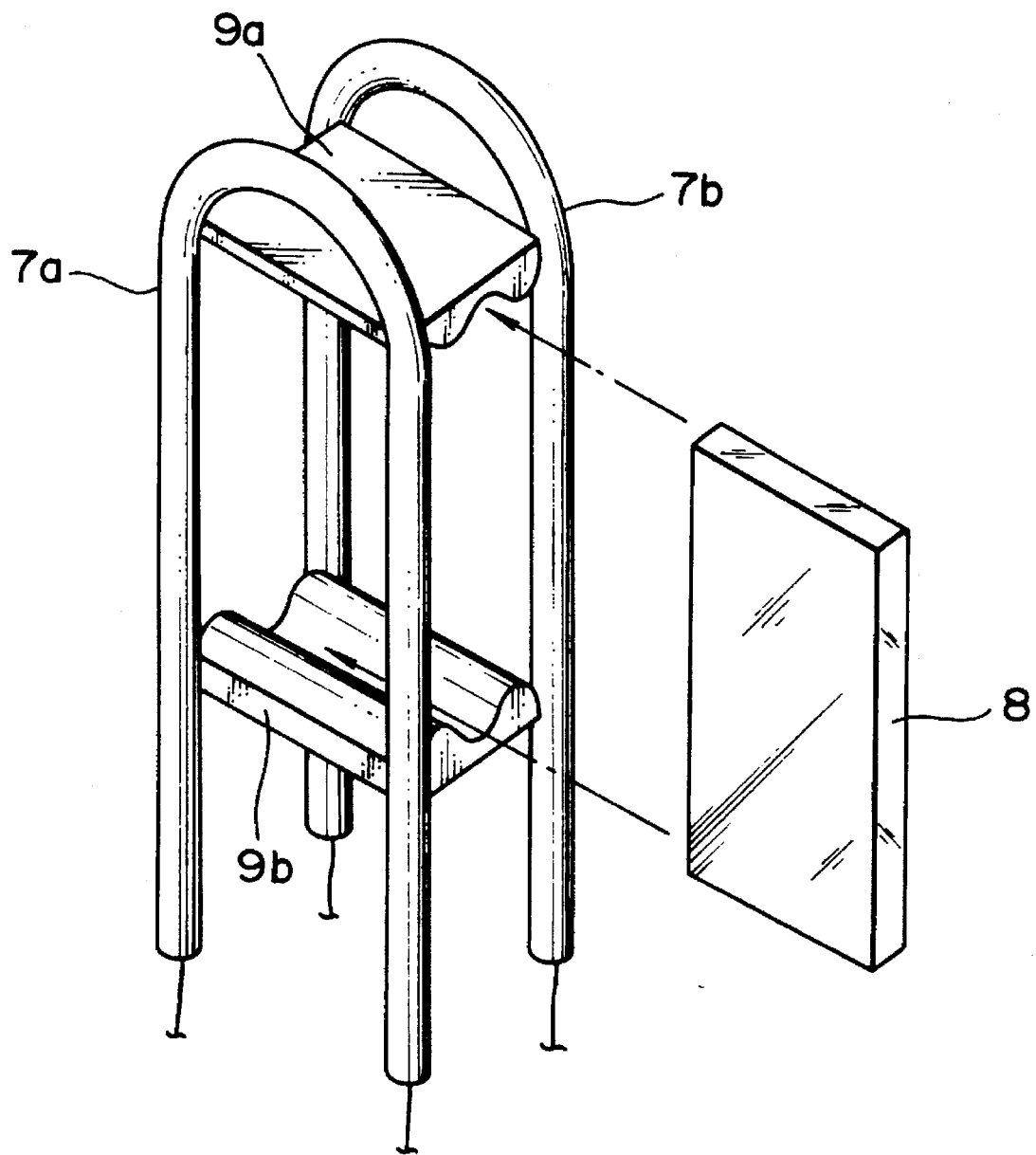
FIG. 2 is a fragmentary perspective view showing a sensor holder of the device shown in FIG. 1.

Referring to FIG. 2, designated as 8 is a CO sensor material according to the present invention. The sensor material 8 is inserted between a pair of opposing grooves of upper and lower support plates 9a and 9b fixed to a pair of U-shaped pipes 7a and 7b. A resistor wire extends inside of each of the pipes 7a and 7b.

As shown in FIG. 1, the above assembly is disposed in a glass cell 6 with the resistor wires being coupled with lead wires 13 extending from a power source 14. Designated as 10 is a temperature sensor for measuring the temperature of the atmosphere surrounding the sensor 10. The temperature sensor 10 is in electrically coupled with a controller 15 through a lead wire 10a. Thus, the inside space of the glass cell 6 can be electrically heated by the resistor wires in the pipes 7a and 7b and maintained at a desired temperature by the operation of the controller 15. The glass cell 6 has an inlet conduit 11 through which gas to be measured is fed to the cell 6 at a predetermined rate and an outlet conduit 12 through which the gas is discharged.

Designated as 1 is a light source from which an optical fiber 2a extends to a position adjacent to the glass cell 6. The light from the light source 1 is thus passed through the optical fiber 2a and a terminal 3 thereof and is introduced through a diaphragm 4 and a collimating lens (not shown) into the glass cell 6. The incident light is then passed through the sensor material 8 and a light collecting lens 18 to a light receiving terminal 18 of an optical fiber 2b. Thus, the light transmitted through the sensor material 8 is received by a light quantity measuring means 19 including a photoelectric converter. Designated as 20 is a spectrum analyzer used for measuring the transmittance of light with a specific wave length.

The following examples will further illustrate the present invention.

Example 1 n-Butanol (2.15 g) was mixed with 2.51 g of an octanoic acid solution containing 60 mg of nickel and 121 mg of cobalt. The resulting mixed solution was applied to a square glass plate of 18 mm×18 mm×0.1 mm with a spin coater. Thus, while rotating the glass plate secured on the spin coater at a rate of 6,000 rpm, 2.0 ml of the mixed solution was applied to the glass plate through 100 seconds. The glass plate was removed from the coater and allowed to stand at room temperature for 20 hours for drying the coated layer. The glass layer bearing the dried layer was placed in an electric oven and heated to 400° C. for 1 hour and then maintained at that temperature for two hours to calcine the layer. The glass plate was then allowed to cool at room temperature, thereby obtaining a composite CO sensor material having a Ni-Co oxide film (Ni/Co atomic ratio: 1:2) provided on the glass plate.

Example 2

Example 1 was repeated in the same manner as described except that the amounts of the Ni and Co were varied so that a composite CO sensor material having a Ni-Co oxide film (Ni/Co atomic ratio: 9:1) was obtained.

Comparative Examples 1 and 2

Example 1 was repeated in the same manner as described except that no cobalt was used (Comparative Example 1) or no nickel was used (Comparative Example 2), thereby obtaining comparative sensor materials having a NiO film (Comparative Example 1) and a $Co_3O_4$ film (Comparative Example 2).

Each of the thus obtained sensor materials was tested for the CO detecting characteristics using a device as shown in FIG. 1 under the following conditions:

| | |
|---|---|
| Temperature of the atmosphere adjacent to the sensor 8: | about 300° C. |
| Light source 1: | haogen lamp emitting light of wave length of 350–800 nm, mainly 400–650 nm |
| Glass cell 6: | 180 ml glass cell |
| Light quantity measuring | photo power meter* |
| Sample gas (I): | air |
| Sample gas (II): | air conditioning 1.0% by volume of CO |

*: Type TQ8210 manufactured by Advantest Inc. This power meter is of a type in which the quantity of light is indicated as a quantity of electricity using a photodiode.

The measurement of the light quantity transmitted from the sensor material 8 was performed 30 minutes after the sample gas had been continuously fed to the glass cell 6 at a predetermined flow rate. The results are summarized in Table 1 below. In Table 1, the term "difference in transmittance" refers to the difference in light quantity as measured by the power meter 19 between the case where sample gas (I) was fed to the glass cell 6 and the case where sample gas (II) was fed to the glass cell 6 and the term "ratio of absorbance" refers to a ratio of the absorbance in the case sample gas (II) was fed to the glass cell 6 to the absorbance in the case where sample gas (I) was fed to the glass cell 6.

TABLE 1

| Example No. | Ni:Co | Difference in transmittance (nW) | Ratio of absorbance |
|---|---|---|---|
| Example 1 | 1:2 | 50 | 0.95 |
| Example 2 | 9:1 | 25.5 | 0.74 |
| Comparative Example 1 | no Co | 18 | 0.91 |
| Comparative Example 2 | no Ni | 16 | 0.92 |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A method of detecting carbon monoxide in an oxygen-containing gas, comprising the steps of:

fixedly securing a sensor within a light permeable cell, said sensor comprising a transparent substrate, and a metal oxide layer provided over a surface of said substrate and containing nickel oxide and cobalt oxide in an amount providing an atomic ratio Ni/Co of 99:1 to 1:2;

feeding said gas through said sensor-containing cell;

irradiating said cell with light having a wave length of 350–1,500 nm while maintaining said sensor at a temperature of 200°–350° C., such that said light passes through said sensor contained in said cell; and measuring the transmittance of said light through said sensor by means of a photoelectric device, said measured transmittance being indicative of carbon monoxide in the oxygen-containing gas.

* * * * *

UNITED STATES PATENT AND TRADEMARK OFFICE
CERTIFICATE OF CORRECTION

PATENT NO. : 5,644,116
DATED : July 1, 1997
INVENTOR(S) : NODA et al

It is certified that error appears in the above-indentified patent and that said Letters Patent is hereby corrected as shown below:

In the table at column 4, line 8, "Light quantity measuring" should read --Light quantity measuring means 19:--; and line 10, "air conditioning" should read --air containing--.

Signed and Sealed this

Thirtieth Day of June, 1998

Attest:

BRUCE LEHMAN

Attesting Officer

Commissioner of Patents and Trademarks